United States Patent
Kruse

(10) Patent No.: US 8,603,809 B2
(45) Date of Patent: Dec. 10, 2013

(54) ISOLATED ADULT PLURIPOTENT STEM CELLS AND METHODS FOR ISOLATING AND CULTIVATING THEREOF

(75) Inventor: Charli Kruse, Herrnburg (DE)

(73) Assignee: Fraunhofer Gesellschaft zur Forderung der angewandten Forschung e. V. (DE)

( * ) Notice: Subject to any disclaimer, the term of this patent is extended or adjusted under 35 U.S.C. 154(b) by 1038 days.

(21) Appl. No.: 10/820,430

(22) Filed: Apr. 8, 2004

(65) Prior Publication Data

US 2005/0014254 A1    Jan. 20, 2005

(30) Foreign Application Priority Data

Jun. 23, 2003 (DE) .................................. 103 28 280

(51) Int. Cl.
*C12N 5/00* (2006.01)
*C12N 5/02* (2006.01)

(52) U.S. Cl.
USPC .......................................... 435/325; 435/378

(58) Field of Classification Search
USPC ................................................ 435/325, 378
See application file for complete search history.

(56) References Cited

U.S. PATENT DOCUMENTS

| | | | |
|---|---|---|---|
| 6,436,704 B1 * | 8/2002 | Roberts et al. ................. | 435/366 |
| 6,638,501 B1 | 10/2003 | Bjornson et al. | |
| 2004/0101962 A1 | 5/2004 | Kremer et al. | |
| 2004/0208857 A1 | 10/2004 | Bader et al. | |

FOREIGN PATENT DOCUMENTS

| | | |
|---|---|---|
| DE | 100 61 334 A1 | 6/2002 |
| DE | 102 14 095 C1 | 9/2003 |
| DE | 102 31 655 A1 | 2/2004 |
| WO | WO 02/057430 A2 | 7/2002 |
| WO | WO 02/064748 A2 | 8/2002 |

OTHER PUBLICATIONS

Pera et al., 2000, Journal of Cell Science, 113: 5-10.*
Henningson, et al., 2003, Journal of Allergy and Clinical Immunology, 111, supplement 2: 745, 753.*
Jiang et al., 2002, Nature, 418: 41-49.*
Zuk et al., 2002, Molecular Biology of the Cell, 13: 4279-4295.*
Schneider et al., 2001, Am. J. Physiol. Cell. Physiol., 281: C532-0543.*
Kruse et al., 2004, Appl. Phys. A, 79: 1617-1624.*
Apte et al., 1998, Gut, 43: 128-133.*
Bachem et al., 1998, Gastroenterol., 115: 421-432.*
Li et al., 2003, Nature Medicine, 9: 1293-1299.*
Stem Cell Basics [online], 2008 [retrieved on Apr. 20, 2008]. Retrieved from the Internet:< URL: http://http://stemcells.nih.gov/info/basics/basics3.asp>, pp. 1-4.*
Clarke et al., 2000, Science, 288: 1660-1663.*
Pittenger et al., 1999, Science, 284: 143-147.*
Abraham et al., "Insulinotropic hormone glucagon-like peptide-1 differentiation of human pancreatic islet-derived progenitor cells into insulin-producing cells," *Endocrinology*, 2002; 143:3152-61.
Apte et al., "Periacinar stellate shaped cells in rat pancreas: identification, isolation, and culture," *Gut*, 1998; 43:128-33.
Bachem et al., "Identification, culture, and characterization of pancreatic stellate cells in rats and humans," *Gastroenterol*, 1998; 115:421-432.
Birth et al., "Isolation, Kultur und Charakterisierung von adulten pluripotenten Stammzellen aùs dem Pankreas," *Chirurgisches Forum*, 2004, Band 33: 405-407.
Bonner-Weir et al., "In vitro cultivation of human islets from expanded ductal tissue," *Proc Natl Acad Sci*, 2000; 97:7999-8004.
Abstract of Bouwens, "Transdifferentiation versus stem cell hypothesis for the regeneration of islet beta-cells in the pancreas," *Microsc Res Tech*,. 1998; 43(4):332-6.
Brazelton et al., "From marrow to brain: expression of neuronal phenotypes in adult mice," *Science*, 2000; 290:1775-9.
Abstract of Elsässer et al., "Repetitive cerulein-induced pancreatitis and pancreatic fibrosis in the rat," *Pancreas*, 1992;7:385-90.
Abstract of Elsässer et al., "Time course and cellular source of pancreatic regeneration following acute pancreatitis in the rat," *Pancreas*, 1986; 1:421-9.
Frankel, "In search of stem policy," *Science*, 2000; 287:1397.
Grosfils, "Isolation of rat pancreatic acini with crude collagenase and permeabilization of these acini with Streptolysin O," *Res Commun Chem Pathol Pharmacol*, 1993; 79:99-115.
Abstract of Hematti et al., "Absence of donor-derived keratinocyte stem cells in skin tissues cultured from patients after mobilized peripheral blood hematopoietic stem cell transplantation," *Exp Hematol*, 2002; 30:943-9.
Hwang,et al., *Science*, 303, 1669-1674 (2004).
Abstract of Ikejiri, "The vitamin A-storing cells in the human and rat pancreas," *Kurume Med J*, 1990; 37:67-81.
Jaster et al., "Extracellular signal regulated kinases are key mediators of mitogenic signals in rat pancreatic stellate cells," *Gut 2002*; 51:579-584.
Jiang et al., "Neuroectodermal differentiation from mouse multipotent adult progenitor cells," *Proc. Natl. Acad. Sci. USA*, 2003; 100:11854-11860.
Jiang et al., "Pluripotency of mesenchymal stem cells derived from adult marrow," *Nature*, 2002; 418:41-49.
Johnstone et al., "In vitro chondrogenesis of bone marrow-derived mesenchymal progenitor cells," *Exp Cell Res*, 1998; 238; 265-72.
Abstract of Kato et al., "Morphological identification of and collagen synthesis by periacinar fibroblastoid cells cultured from isolated rat pancreatic acini," *J Gastroenterol*, 1996; 31:565-71.
Abstract of Kennedy et al., "Pancreatic extracellular matrix alterations in chronic pancreatitis," *Pancreas*, 1987; 2:61-72.
Kopen et al., "Marrow stromal cells migrate throughout forebrain and cerebellum, and they differentiate into astrocytes after injection into neonatal mouse brains," *Proc Natl Acad Sci*, 1999;96; 10711-6.
Abstract of Korbling et al., "Hepatocytes and epithelial cells of donor origin in recipients of peripheralblood stem cells," *N Engl J Med*, 2002; 346(10): 738-46.

(Continued)

*Primary Examiner* — Thaian N Ton

(74) *Attorney, Agent, or Firm* — Caesar, Rivise, Bernstein, Cohen & Pokotillow, Ltd.

(57) ABSTRACT

This invention relates to isolated pluripotent adult stem cells which are obtained from exocrine glandular tissue as well as methods of isolating and culturing these pluripotent stem cells.

26 Claims, 8 Drawing Sheets

(56) References Cited

OTHER PUBLICATIONS

Abstract of Krause et al., "Multi-organ, multi-lineage engraftment by a single bone marrow-derived stem cell," *Cell*, 2001; 105:369-77.

Kruse et al., "Pluripotency of adult stem cells derived from human and rat pancreas," *Appl. Phys. A* (2004); 79:1617-1624.

Kruse et al., "Evidence for a novel cytoplasmic tRNA-protein complex containing the KH-multidomain protein vigilin," *Biochem J*, 1996; 320:247-252.

Kruse et al., "Isolation, long-term culture, and characterization of rat pancreatic fibroblastoid/stellate cells," *Pancreas*, 2001; 23:49-54.

Lagasse et al., "Purified hematopoietic stem cells can differentiate into hepatocytes in vivo," *Nature Med.*, 2000; 6:1229-1234.

Mezey et al., "Turning blood into brain: cells bearing neuronal antigens generated in vivo from bone marrow," *Science*, 2000; 290:1779-82.

Orkin et al., "Biomedicine: Stem-cell competition," *Nature*, (2002); 418: 25-27.

Plenz et al., "Expression of vigilin in chicken cartilage and bone," *Cell Tissue Res*, 1993; 273:381-389.

Poulsom et al., "Adult stem cell plasticity," *J Pathol*, 2002; 197:441-56.

Abstract of Ramiya et al., "Reversal of insulin-dependent diabetes using islets generated in vitro from pancreatic stem cells," *Nat Med*, 2000; 6:278-82.

Romero-Ramos et al., "Neuronal differentiation of stem cells isolated from adult muscle," *J Neurosci Res*, 2002; 69:894-907.

Abstract of Sanchez-Rarnos et al., "Adult bone marrow stromal cells differentiate into neurol cells in vitro," *Exp Neurol*, 2000; 164:247-56.

Abstract of Saotome et al., "Morphological and immunocytochemical identification of periacinar fibroblast-like cells derived from human pancreatic acini," *Pancreas*, 1997;14:373-82.

Schneider et al., "Identification of mediators stimulating proliferation and matrix synthesis of rat pancreatic stellate cells," *Am J Physiol Cell Physiol*, 2001; 281:532-543.

Sekiya et al., "In vitro cartilage formation by human adult stem cells from bone marrow stroma defines the sequence of cellular and molecular events during chondrogenesis," *Proc Natl Acad Sci*, 2002; 99:4397-402.

Shinji et al., "Establishment of a novel collagenase perfusion method to isolate rat pancreatic stellate cells and investigation of their gene expression of TGF-beta1, type 1 collagen, and CTGF in primary culture or freshly isolated cells," *Acta Med Okayama*, 2002; 56:211-218.

Abstract of Sparmann et al., "Generation and characterization of immortalized rat pancreatic stellate cells," *Am. J. Physiol. Gastrointest. Liver Physiol.*, 2004; 287(1):6211-9.

Abstract of Wobus et al., "Specific effects of nerve growth factor on the differentiation pattern of mouse embryonic stem cells in vitro," *Biomed. Biochim. Acta*, 1988; 47:965-973.

Woodbury et al., "Adult rat and human bone marrow stromal cells differentiate into neurons," *J Neurosci Res*, 2000; 61:364-70.

Yang et al., "In vitro transdifferentiation of adult hepatic stem cells into pancreatic endocrine hormone-producing cells," *Proc Natl Acad Sci*, 2002; 99:8078-83.

Yates et al., "Early shifts in gene expression during chondroinduction of human dermal fibroblasts," *Exp Cell Res*, 2001; 265:203-211.

Zulewski et al., "Multipotential nestin-positive stem cells isolated from adult pancreatic islets differentiate ex vivo into pancreatic endocrine, exocrine, and hepatic phenotypes," *Diabetes*, 2001; 50:521-33.

Kajahn, J., et al., Skin-derived human adult stem cells surprisingly share many features with human pancreatic stem cells. Eur. J. Cell Biol. (2007).

Wiese et al. Cell Mol Life Sci. Oct. 2004; 61(19-20): p. 2510, abstract.

Peck, A.B. et al., Generation of islets of Langerhans from adult pancreatic stem cells, J. Hepatobiliary Pancreat Surg., 2002, vol. 9, pp. 704-709.

\* cited by examiner

ISOLATED ADULT PLURIPOTENT STEM CELLS AND METHODS FOR ISOLATING AND CULTIVATING THEREOF

The present invention relates to adult pluripotent stem cells and a method of isolating and culturing the same.

BACKGROUND OF THE INVENTION

Stem cells are cells having the ability to divide to an unlimited extent and to differentiate under suitable circumstances and/or through suitable stimuli to form different types of cells. Stem cells have the potential to develop into cells with a characteristic shape and specialized functions.

Because of their different potential for differentiating into different cell types, a distinction has been made so far between embryonal stem cells and adult stem cells. It is the general consensus that the potency of stem cells decreases with their development from the fertilized egg cell to the embryonal stage to the adult organism. According to this property, the fertilized egg cell is referred to as totipotent, embryonal stem cells are referred to as pluripotent and adult stem cells are referred to as multipotent.

Totipotent cells are cells from which a complete organism can develop. In addition to the fertilized egg cell, these also include the cells of the early embryonal phase. Pluripotency is understood to refer to the fact that the embryonal stem cells which are typically obtained from the internal cell mass of disaggregated blastocytes are capable of differentiating into cells of all three germ layers—mesoderm, endoderm and ectoderm.

According to learned opinion so far, however, adult stem cells are only multipotent, i.e., they are capable of differentiation only to a lesser extent. Thus tissue-specific stem cells should be capable only of differentiation into cells of the same tissue type. In recent years, this view had to be corrected at least in part because investigations with adult stem cells obtained, for example, from bone marrow (WO 02/064748) or from regenerative tissue (WO 02/057430) have proven that under certain conditions, e.g., transplantation into a target tissue, culturing on a feeder cell layer and/or culturing in the presence of specific growth factors, differentiation of individual stem cells to form cell types of different germ layers is also achievable. However, these adult stem cells are still not equivalent to the embryonal stem cells with regard to self-renewal ability and differentiation potential. In particular the stability of these cell lines in long-term culturing is not ensured and the cells have a tendency to spontaneous differentiation and under some circumstances even to malignancy to develop tumor cells. Furthermore the rate of proliferation declines significantly with longer culturing.

Thus in view of the ethical objections with regard to embryonal stem cells, there is still a great deal of interest in new adult stem cells with the greatest possible differentiation potential and with properties equivalent to those of the embryonal stem cells.

Therefore the object of this invention is to provide new adult stem cells which no longer have any significant differences in their self-renewal ability and differentiation potential in comparison with embryonal stem cells and which can be referred to as actually pluripotent. One related object is to provide new and especially simple methods of isolation and culturing of adult pluripotent stem cells and differentiated cells derived thereof. Another related object is to provide new pharmaceutical compositions and methods of treatment of various disease states using pluripotent stem cells.

These objects are achieved according to this invention by providing isolated pluripotent adult stem cells which have been obtained from exocrine glandular tissue as well as the inventive methods of isolating and culturing these stem cells and differentiated cells derived therefrom and by providing pharmaceutical compositions and methods of treatment using the inventive stem cells and/or differentiated cells derived therefrom.

SUMMARY OF THE INVENTION

Adult stem cells with varying potentials for differentiation have already been found in numerous tissues. Presumed stem cells have already been isolated from the endocrine insulin-producing glandular tissue of the pancreas, but cells that could be characterized as stem cells have not previously been isolated from any exocrine glandular tissue.

It is therefore extremely surprising that the inventive method makes it possible for the first time to produce adult stem cells by a particularly simple method from exocrine glandular tissue, which adult stem cells no longer have any significant differences from embryonal stem cells with regard to their self-renewal ability and their differentiation potential and which can be called pluripotent.

The exocrine glandular tissue used as the source material is preferably obtained from a vertebrate, e.g., a fish, amphibian, reptile, bird or mammal, especially preferably from a primate and in particular from a human.

The exocrine glandular tissue used according to this invention may be derived from an adult organism, a juvenile organism or nonhuman fetal organism, preferably a postnatal organism. The term "adult" as used in the present patent application thus refers to the stage of development of the source tissue and not that of the donor organism from which the tissue originates. "Adult" stem cells are nonembryonal stem cells.

The exocrine glandular tissue is preferably obtained from a salivary gland, lacrimal gland, sebaceous gland, sudoriferous gland, glands of the genital tract including the prostate or gastrointestinal tissue including the pancreas or secretory tissue of the liver. In a greatly preferred embodiment, this is acinar tissue. The acinar tissue especially preferably is derived from the pancreas, the parotid gland or the mandibular gland.

The stem cells provided by the method according to this invention are easily isolated and kept in an undifferentiated state in a stable long-term culture without a feeder cell layer or specific additive. The term feeder cells as used in the present application refers to all cells that promote the growth of the cells actually to be cultured by releasing growth factors and/or supplying an extracellular matrix and/or preventing differentiation of the stem cell culture.

In stem cell cultures of the present inventors, the cells have retained their self-renewal ability and their capability for unrestricted division after so far more than 25 passages over a period of one year and the cultures are still stable. Only a very small portion of the stem cells (approximately 3%) undergo spontaneous differentiation and are separated with the old medium with no problem when changing the medium.

In addition, the stem cells produced in this way can be stored frozen at the temperature of liquid nitrogen and retain their differentiability and vitality unchanged.

The inventive adult stem cells can be stimulated easily to differentiate without adding any specific growth factors or differentiation factors; this is accomplished by culturing them under spatial conditions which ensure three-dimensional contact of the cells. In a preferred embodiment, these conditions include culturing in hanging drops such as the method already described starting with embryonal stem cells (Wobus et al., *Biomed. Biochim. Acta* 47:965-973, 1988). This method is described in greater detail below in the examples. However, it is self-evident that alternative culturing methods which ensure the desired three-dimensional contact of the cells and which are known and available to those skilled in the art may also be used. Examples of such alternative methods include culturing in moving suspension culture, culturing in an electromagnetic field cage or by the laser tweezer method or culturing on surfaces to which the cells have little or no adhesion. Such surfaces may be, for example glass, polystyrene or surfaces treated with an anti-adhesion layer, e.g., PTFE-coated surfaces or poly-HEMA-coated surfaces.

Under these conditions, three-dimensional cell structures or cell aggregates develop spontaneously; these have been described by the present inventor as "organoid bodies" based on the term "embryoid bodies" which is already used for embryonal stem cells. These organoid bodies may be transferred to suspension culture or adhesion cultures and cultured further. If there is an adequate nutrient supply, these organoid bodies continue to grow and may reach diameters of a few millimeters or more. These large organoid bodies have a tissue-like structure and in this stage are also referred to as "tissue bodies" to distinguish them from the simple cell aggregates.

If the organoid bodies are introduced into a surface culture again, a cellular monolayer is formed from out-growing single cells, leading to multilayer regions from which secondary organoid bodies having comparable properties like those of the primary organoid bodies are formed spontaneously. The inventive organoid bodies may be stored frozen, e.g., at the temperature of liquid nitrogen without losing their viability, reproductive ability, growth ability or differentiability.

Cells grown or isolated from the organoid bodies can differentiate into the various cell types of all three germ layers. For differentiation, no differentiation factors are necessary and also the cells have not to be transplanted in order to differentiate. However, it may be advantageous to use such differentiation factors to produce large quantities of a certain cell type in a controlled fashion. Such differentiation factors are known in the state of the art and include for example bFGF ("basic fibroblast growth factor") for increased production of cardiac cells and fibroblasts, VEGF ("vascular endothelial growth factor"), DMSO and isoproterenol, fibroblast growth factor 4 (FGF4), hepatocyte growth factor (HGF) for increased production of cardiac cells and hepatic cells, TGF-beta1 ("transforming growth factor beta1") for increased production of cardiac cells, EGF ("epidermal growth factor") for increased production of dermal cells and cardiac cells, KGF ("keratinocyte growth factor") (sometimes together with cortisone) to form keratinocytes, retinoic acid for increased production of nerve cells, heart cells and kidney cells, beta-NGF ("beta nerve growth factor") for increased production of brain cells, liver cells, pancreas cells and kidney cells, BMP-4 ("bone morphogenic protein 4") and activin A for forming mesodermal cells in general, but this invention is not limited to these cell types.

Differentiated cells that can be obtained from the inventive pluripotent stem cells include bone cells (osteoblasts and osteoclasts), chondrocytes, adipocytes, fibroblasts (e.g., skin and tendon fibroblasts), muscle cells, endothelial cells, epithelial cells, hematopoietic cells, sensory cells, endocrine and exocrine glandular cells, glial cells, neural cells, oligodendrocytes, blood cells, intestinal cells, heart, lung, liver, kidney or pancreas cells but are not limited to these cells.

The resulting differentiated cell types can be identified and characterized by histological, immunocytochemical and electron microscopic techniques.

The inventive adult pluripotent stem cells and/or differentiated cells and organoid bodies derived therefrom have a broad spectrum of possible applications in medical and non-medical fields. For example, the cells may be administered to an animal or human patient to treat an injury or a disease state.

The disease state to be treated may be any disease state which can be expected to be treated successfully with stem cells. Such disease states may include, for example, a tumor, a lung disease, a liver disease, a kidney disease, a connective tissue disease, a cardiovascular disease, a metabolic disease, a neurodegenerative disease, an autoimmune disease, anemia, hemophilia, diabetes, ischemia, inflammation, an infectious disease, a genetic defect or transplant rejection as well aging processes.

Preferably the cells administered are autologous, i.e., they originate from the patient to be treated in order to avoid a rejection reaction. The treatment may consist of for example the fact that the cells administered differentiate in vivo to assume the function of a damaged or a missing organ or tissue in the body of a patient. The organ or tissue may be selected from, for example, bone marrow, blood, spleen, lung, kidney, bladder, intestine, brain, fatty tissue, connective tissue, muscle tissue, heart, blood vessels, pancreas, CNS, peripheral nervous system, skin and especially the mucous membranes.

In a preferred embodiment, the treatment strengthens the patient's immune system or restores it. In another embodiment, the treatment consists of bringing the blood or another body fluid of a patient in contact with the stem cells or cells derived therefrom, e.g., liver or kidney cells, outside of the patient's body in order to, e.g., remove toxins from the body fluid or otherwise subject it to a therapeutic or diagnostic treatment and then the body fluid is returned to the patient's body.

The inventive stem cells administered in this way in a therapeutical method may also serve as a safe vehicle for a therapeutic agent. The therapeutic agent may be for example DNA, RNA, a protein or a peptide or a low-molecular pharmaceutical drug.

In particular the stem cells may be genetic engineered in order to have certain properties and then used for gene therapy. Such properties may include for example reduced antigenicity, production of desired DNA, RNA, proteins, lack of production of unwanted DNA, RNA, proteins, etc.

The cells may be administered by any method which is known in the state of the art and is suitable for this purpose. Suitable methods include but are not limited to local injection, systemic injection, parenteral administration, oral administration or intrauterine injection into an embryo.

As a rule, the stem cells or differentiated cells derived therefrom used for the treatment will be present in a pharmaceutical composition. Such a pharmaceutical composition may contain in addition to the cells a physiologically acceptable matrix or a physiologically acceptable vehicle. The type of matrix and/or vehicle will depend among other things on the intended route of administration. Suitable matrices and/or vehicles are known in the state of the art.

Furthermore the pharmaceutical composition may optionally contain other suitable vehicles or active ingredients.

Another possible use is the use of the stem cells, stem cell cultures, the organoid bodies, or the differentiated cells obtained therefrom for the development of tissue-like or organ-like multicellular systems in vitro. In a preferred embodiment, the multicellular systems include different types of cells. These multicellular systems can then be transplanted, for example, or used extracorporeally, e.g., for hemodialysis or for production of desired substances.

Another possible use is the use of the stem cells, stem cell cultures, the organoid bodies, the differentiated cells or multicellular systems obtained therefrom as an in vitro system for testing chemicals, in particular for screening pharmaceutical drugs or cosmetics and/or for analyzing the effect of known or potential active ingredients or toxins or mutagens on the particular cells. This effect may be for example a change in the proliferation ability, differentiation ability or viability of the cells.

Another possible use is providing complex cellular systems for analysis of cellular interactions.

Another possible application is use of the differentiated cells obtained from the stem cells for production of desired substances in vitro.

A special application for nonhuman adult stem cells is the use of the adult stem cells or differentiated cells obtained therefrom for therapeutic or reproduction cloning. For example the adult stem cells or differentiated cells derived therefrom or cell nuclei isolated therefrom are introduced into enucleated nonhuman oocytes and the oocytes are cultured under conditions which lead to the development of blastocytes. Then either embryonal stem cells are obtained from these blastocytes and then can be induced to differentiate into a desired cell type by known methods (therapeutic cloning) or the blastocytes can be made to develop into an embryo which can be implanted into a female animal and then be born naturally after the corresponding gestation period (reproductive cloning).

In one embodiment of this invention, the stem cells or organoid bodies derived therefrom or differentiated cells are made available in the form of a kit. Such a kit may contain the cells as such or as a pharmaceutical composition as defined above. Furthermore, the kit may also include other substances, e.g., for administration of the cells or reagents, e.g., reagents for culturing the cells or diagnostic reagents.

DETAILED DESCRIPTION OF PREFERRED EMBODIMENTS

In an especially preferred embodiment of the present invention, the adult stem cells are obtained from acinar tissue.

Figure 1:
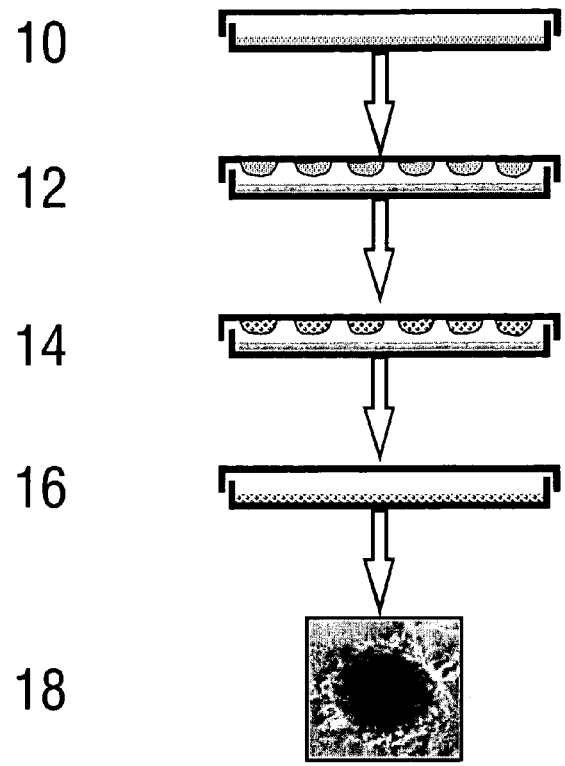
FIG. 1 shows schematically the culturing of the stem cells in surface culture and in hanging drops as well as the formation and further culturing of organoid bodies.
Figure 2:
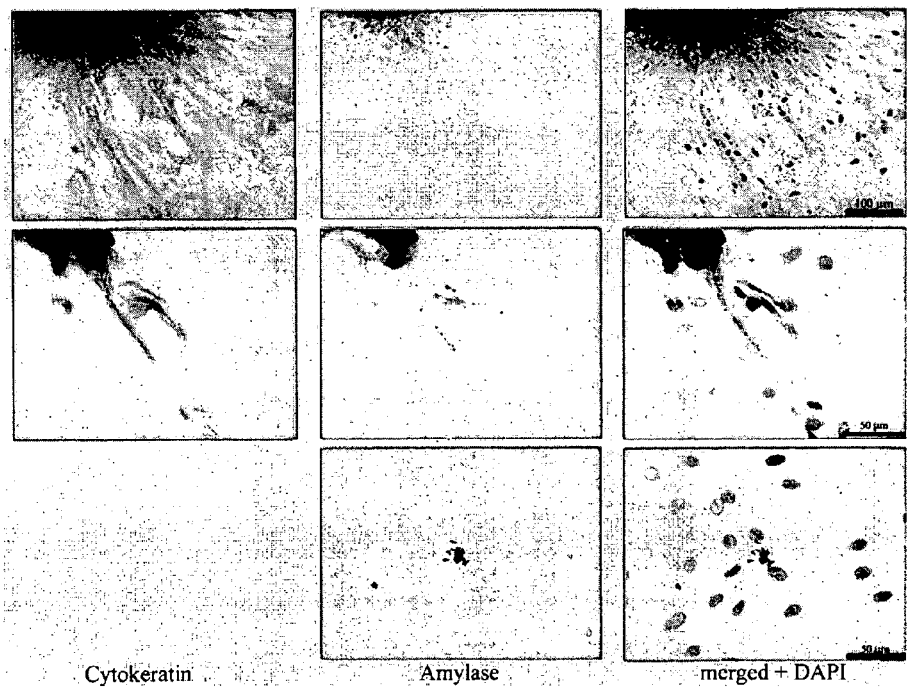
FIG. 2 shows the immunohistological detection of epithelial cells and glandular cells with entodermal properties produced from the inventive stem cells from rat pancreas. These cells were stained with antibodies to cytokeratin and amylase. In addition the cell nuclei were stained with DAPI.
Figure 3:
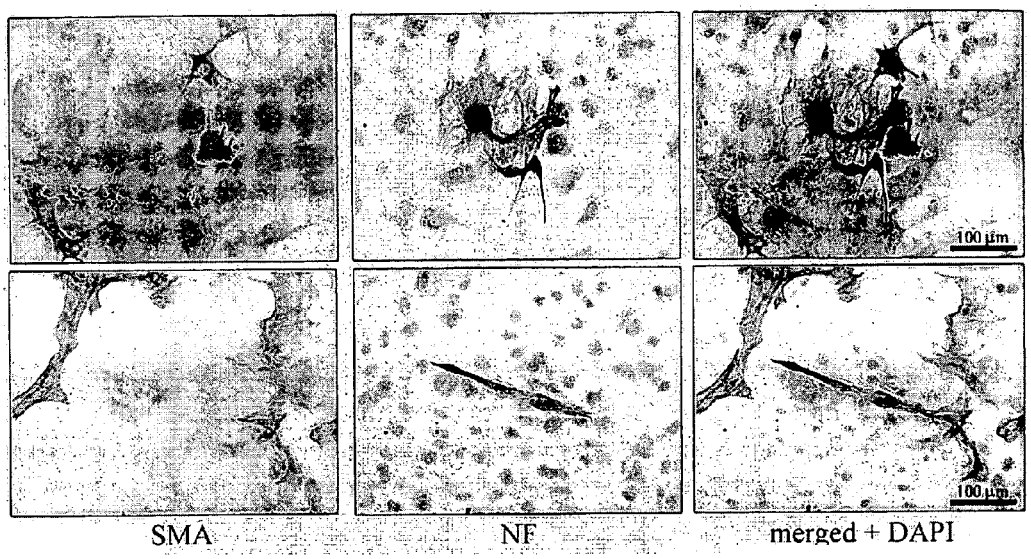
FIG. 3 shows immunohistological detection of differentiated muscle cells with mesodermal and neural cells with ectodermal properties produced from the inventive stem cells from rat pancreas. These cells have been stained with antibodies to α-smooth-muscle actin (SMA) and neurofilament (NF). In addition the cell nuclei were stained with DAPI.
Figure 4:
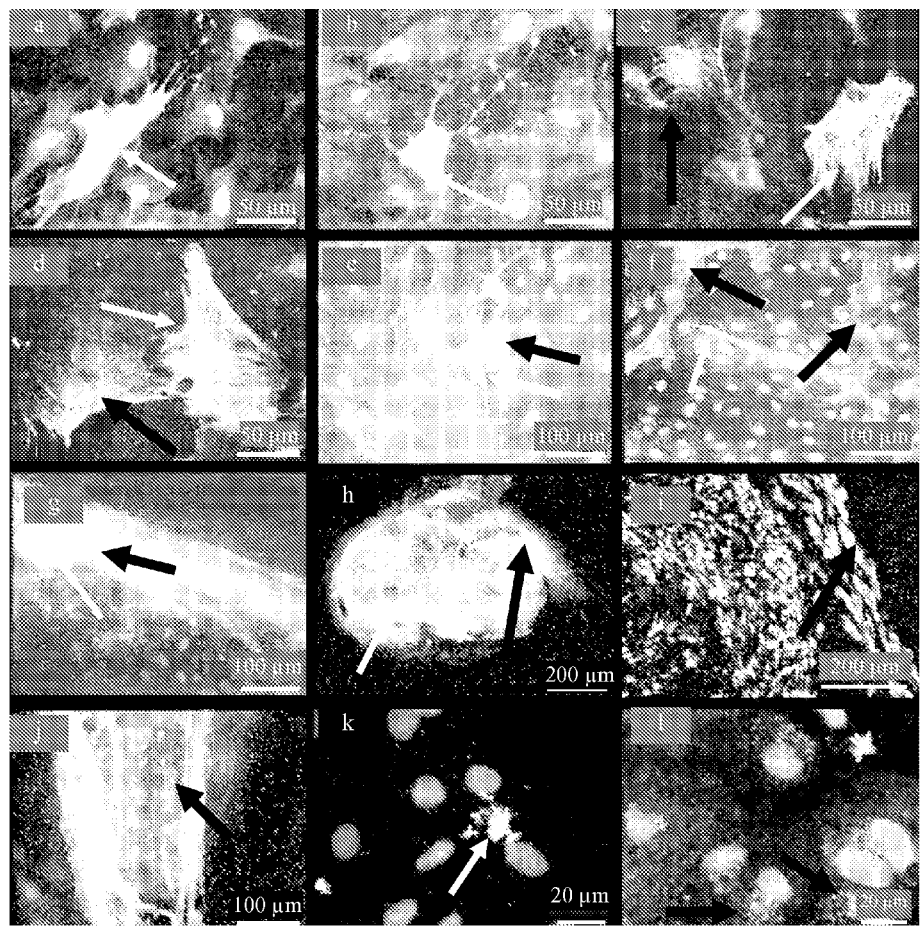
FIG. 4 shows the expression of markers of neural, glial and smooth muscle cells as well as of amylase and insulin.
- a, b: PGP 9.5-labeled neural cells show multipolar processes that display numerous varicosities c, d: The neurofilament apparatus (light arrows, marked in green on the original photo) extends through the pericaryon into the cytoplasmic processes. GFAP-immunoreactive glial cells (dark arrows, marked in red in the original photo) are in close proximity. e, f: α-SMA-labeled cells (dark arrows, red in the original) and NF-labeled nerve cells (light arrows, green in the original) form a primitive neuromuscular network (e) with contacts being established over considerably long distances (f). g: Immunostaining of GFAP (dark arrows, red in the original) and NF (light arrows, green in the original) in three-week-old organoid bodies with concentrations of neural cells and glial cells. h: Immunostaining of α-SMA (dark arrows, red in the original) and NF (light arrows, green in the original) in three-week-old organoid bodies in an advanced stage of formation of a neuromuscular network. i, j: In cross sections of eight-week-old organoid bodies, immunoreactive cells for NF were found in direct proximity of cells that were immunoreactive for α-SMA, as is the case in native tissues. k: A subset of cells shows a positive staining for amylase (light arrows, green in the original). The cells containing amylase are grouped in circles, as shown on the basis of the topographic arrangement of their nuclei, and they store the exocrine secret within the apical cell poles and thus demonstrate morphological features of exocrine pancreatic acini. l: Another cellular subset contains granular vesicles with immunoreactivity for insulin. The endocrine product is not homogeneously distributed but instead is stored in a polar pattern. The nuclei are counterstained with DAPI (blue in the original).
Figure 5:
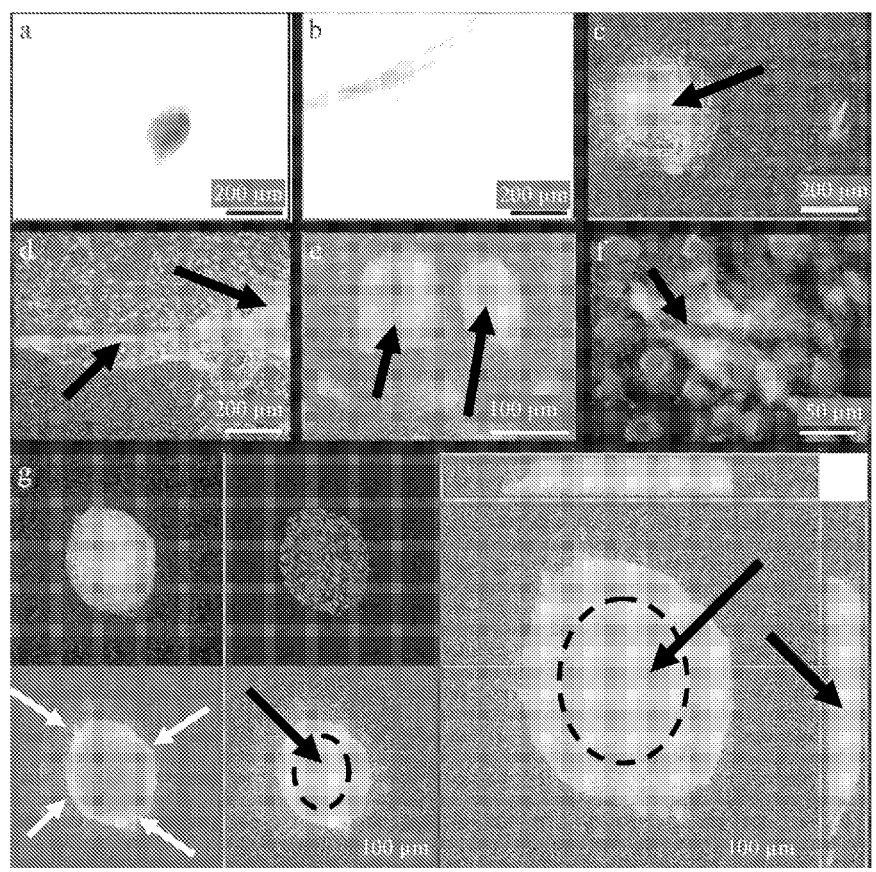
FIG. 5 shows the expression of extracellular matrix components and cytokeratins.
- a, b: Globular (a) and fibrillary (b) deposits of protoglycans were revealed by staining with Alcian blue. c-e: The globular (c) and fibrillary (d) areas are immunoreactive for the cartilage matrix protein collagen II. Densely distributed cells are observed adjacent to the developing extracellular matrix. Two individual cells (e) have a cytoplasmic labeling of collagen II. f: Cells that are immunoreactive for cytokeratins are arranged in clusters. g: Confocal laser scanning microscopy of an OB. The collagen II immunoreactivity (dark arrows, marked red in the original) increases toward the center of the OB. Vigilin-immunoreactive cells (light arrows, marked green in the original) are mainly localized on the outer border of the organoid body, which indicates their high translational activity. The nuclei are counterstained with DAPI.
Figure 6:
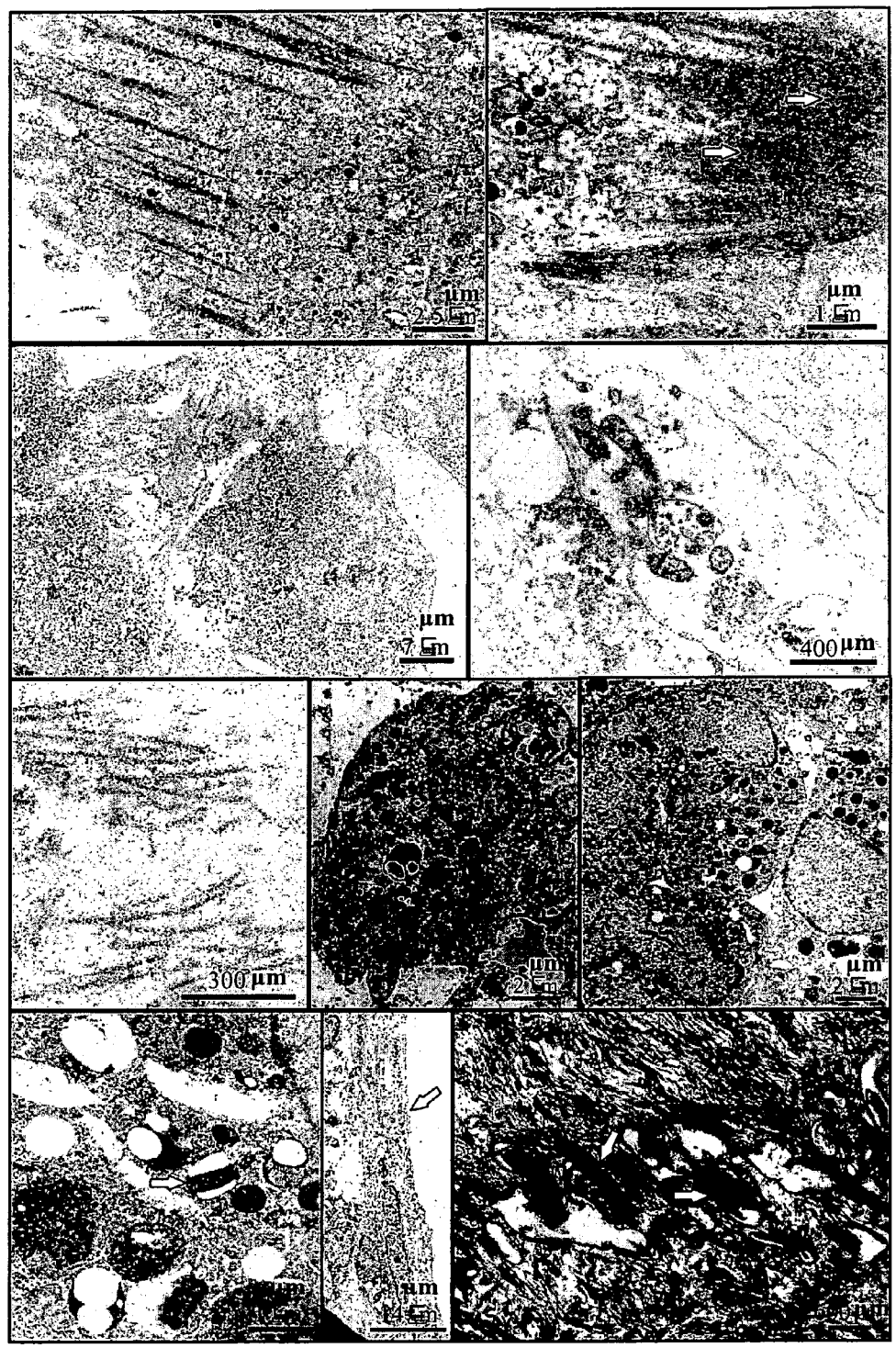
FIG. 6 shows the transmission electron microscopy of differentiated organoid bodies.
- a-c: Smooth muscle cells with myofilaments. The myofilament apparatus extends throughout the cytoplasm in disseminated bundles (a) and shows typical dense bodies (arrows) (b). The myoblasts have stellate cell processes forming a connective network (c). d: Cellular processes with an accumulation of numerous small sized vesicles, most probably corresponding to nerve fiber varicosities. e: Collagen and reticular fibers. The typical striated pattern (periodical bands) of collagen fibers is discernible in longitudinally sectioned fibrils. f-h: Secretory cells displaying electron-dense vesicles. The vesicles do not occupy the entire cytoplasm but instead are stored at one cell pole (f). Secretory cells frequently contact each other to form acinus-like structures (g). A subset of secretory cells contains vesicles (arrow) which correspond to ultrastructure features of endocrine granulae (h), e.g., β-granulae of insulin producing cells. I: Beginning of formation of an epithelial surface (arrow) in eight-week-old organoid bodies. j: Typical cell contacts between keratinocytes and desmosomes (arrows).
Figure 7:
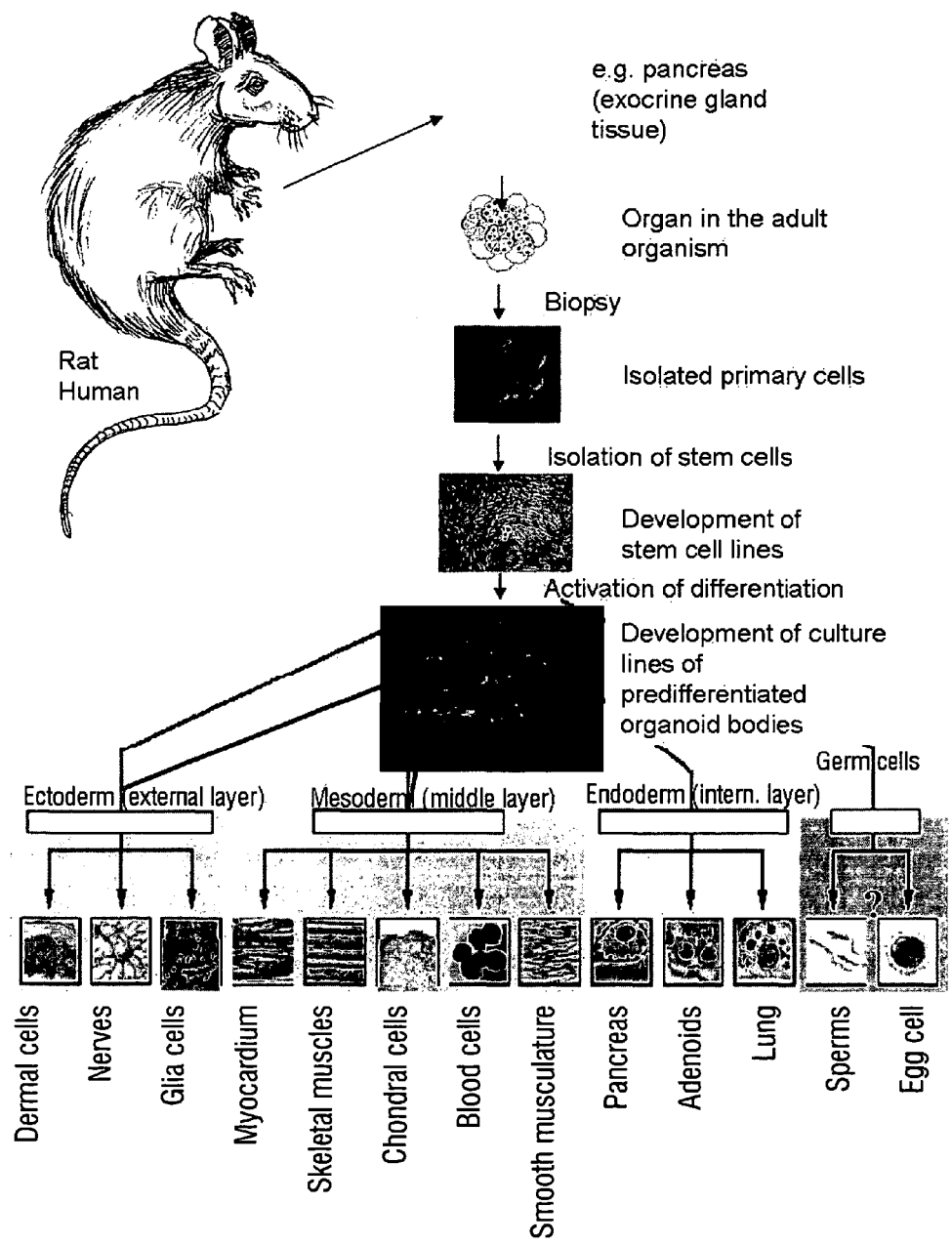
FIG. 7 shows schematically the principal steps in the method according to this invention for isolation and culturing of adult stem cells and producing organoid bodies and a broad spectrum of differentiated cells therefrom.
Figure 8:
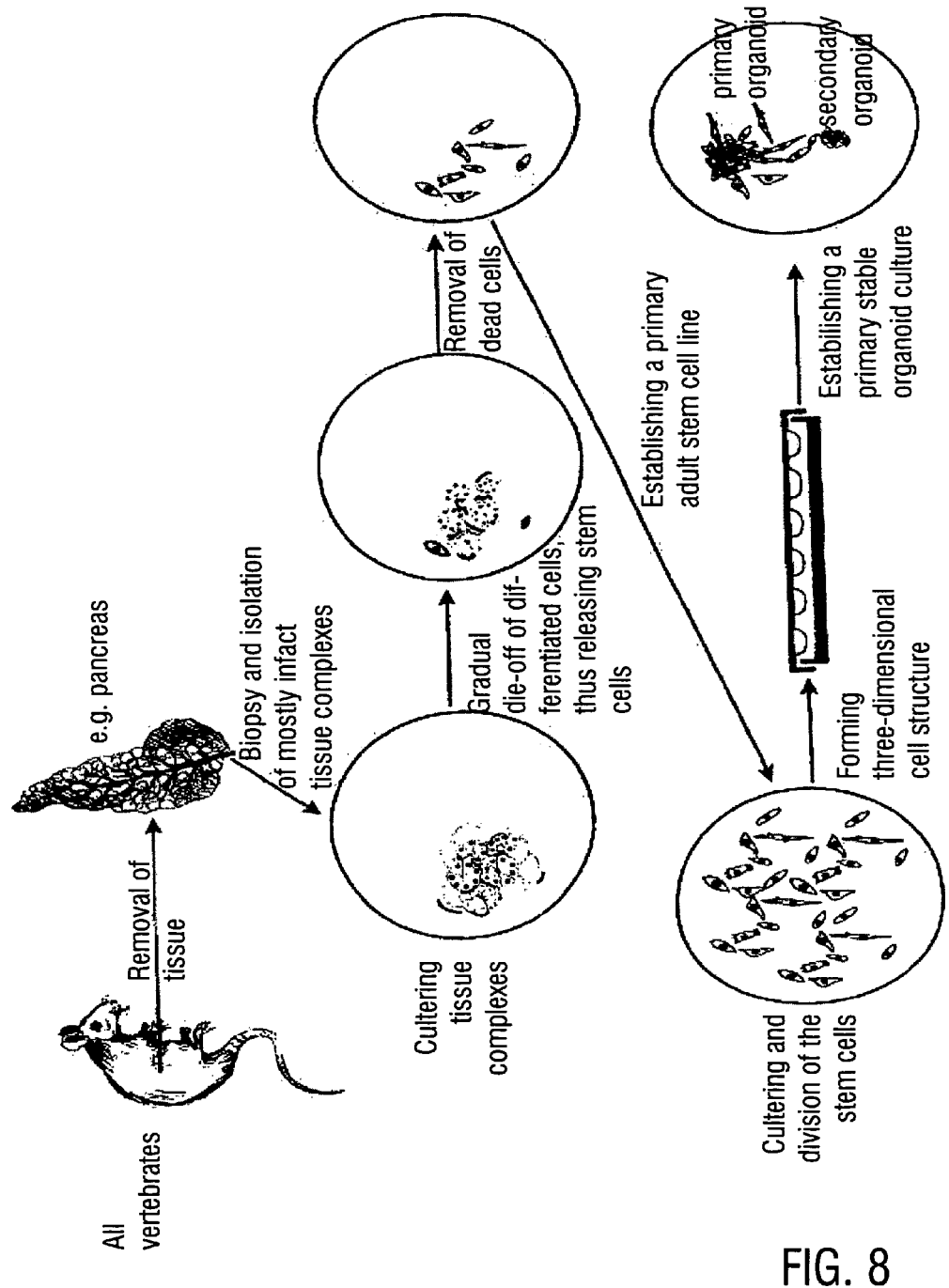
FIG. 8 shows schematically various individual steps of the method according to this invention for isolating and culturing adult stem cells and for producing organoid bodies.
Figure 9:
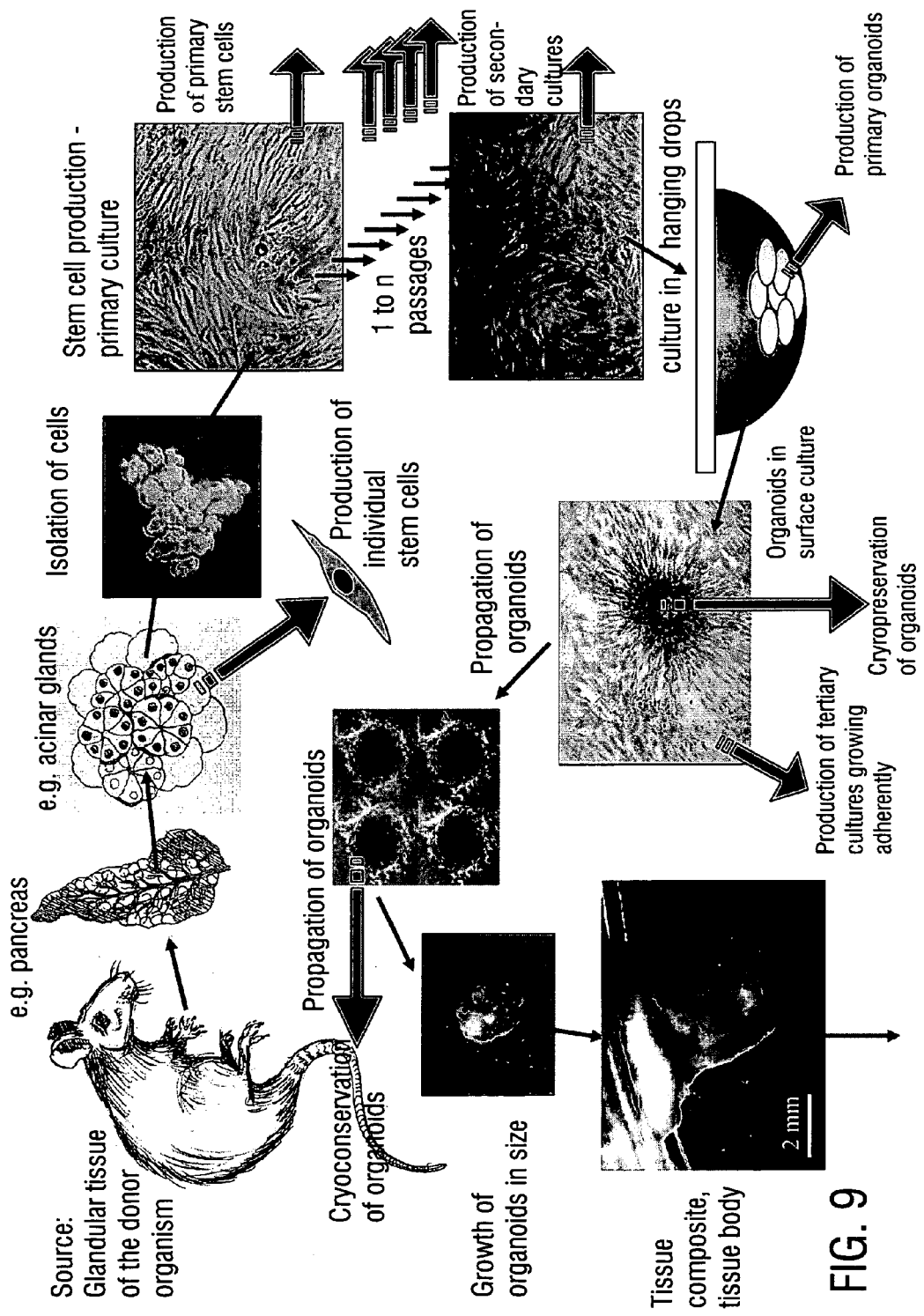
FIG. 9 shows micrographs of the stem cells and organoid bodies after various individual steps of the methods according to this invention for isolation and culturing of adult stem cells and producing organoid bodies.

According to the diagram depicted in FIG. 1, to obtain the cells, acinar tissue, preferably from the parotid gland or the pancreas—is mechanically and enzymatically broken up and cultured (step 10 in FIG. 1). Contrary to the reports by Bachem et al., *Gastroenterol.* 115:421-432 (1998) and Grosfils et al., *Res. Comm. Chem. Pathol. Pharmacol.* 79:99-115 (1993), no tissue blocks from which cells should out-grow are cultured but instead the tissue is divided more finely under the condition that the cell structures of the acini remain largely intact.

For several weeks these cells and cell structures are cultured in culture vessels. Every 2 to 3 days the medium is changed, at which time all the differentiated cells are removed. The cells persisting in culture are undifferentiated cells with an unlimited division ability.

Similar cells have been isolated from the pancreas under the same conditions and have been described as a type of myofibroblast or pancreatic stellate cells (Bachem et al., 1998). Contrary to the cells according to the present invention, however, unrestricted ability to divide could not be observed. In addition, these cells could not be exposed to an unlimited number of passages without losing vitality.

In a second step [12] approximately 400 to 800 cells are cultured in hanging drops in 20 μL medium each. To do so the drops are placed on covers of bacteriological petri dishes, inverted and placed over the petri dish filled with medium so that the drops hang down.

Due to this type of culturing, cell aggregates [14] which are referred to as organoid bodies develop within 48 hours and are transferred to a suspension culture for approximately six days [16]. The partial view in FIG. 1 shows a micrograph of such an organoid body.

The organoid bodies growing in suspension culture form new organoid bodies which induce the formation of new organoid bodies even from single cells. The cells can be frozen as organoid bodies or as single cells and retain their vitality and differentiation potential when frozen.

FIGS. 2 through 6 show micrographs and electron micrographs of differentiated cells obtained from such organoid bodies. For example the formation of a neuromuscular network could be observed: Cells obtained from organoid bodies strongly expressed α-SMA (smooth muscle actin) (FIGS. 4*e-f*). The presence of wide-spread bundles of myofilaments extending through the cytoplasm has been confirmed by electron microscopy (FIGS. 6*a-c*). Furthermore, cells which were immunoreactive for the pan-neuron marker PGP 9.5 and for neurofilaments (NF) have also been identified. The neurofilament apparatus extended from the pericaryon into the radial cytoplasmic processes (FIGS. 4*c, d*). PGP 9.5-immunoreactive cells displayed numerous varicosities along their branched processes (FIG. 4*a, b,* 6*d*) and thus resembled typical morphological features of autonomous nerve fibers. Cells that were immunoreactive for GFAP (glial fibrillary acidic protein) were in close proximity to cells that expressed neural markers (FIG. 4*c, d*). Frequently the filamentary proteins did not extend throughout the entire cytoplasm but instead were limited to regions next to the nerve cells. Furthermore, smooth muscle cells and nerve cells were not randomly scattered but form connected networks with junctions that were easily discernible (FIG. 4*e, f*). Nerve fiber processes extended over considerable distances, contacting adjacent smooth muscle cells as their presumed targets. Thus the two cell types exhibited features of a primitive neuromuscular network based on their topographic arrangement. In three-week-old organoid bodies, an incipient formation of tissue-like structures was observed (FIGS. 4*g-j*). A cluster of fibrous nerve cells was found here in contact with glial cells (FIG. 4*g*) or further developed to a three-dimensional neuromuscular network (FIG. 4*h*) which was confirmed in cross sections of eight-week-old organoid bodies (FIG. 4*i, j*).

Detection of Expression of Exocrine and Endocrine Pancreatic Proteins:

Immunohistochemical stainings have demonstrated that cellular subsets were positive for amylase (FIG. 4*k*). The immunoreaction signal was limited to clearly distinguishable vesicles within the apical cytoplasm. In addition, most cell clusters which were immunoreactive for amylase were arranged in circles with the secretory vesicles assuming a position toward the center which is a morphological arrangement similar to that of exocrine pancreas acini. Other cellular subsets showed immunoreactive for insulin (FIG. 4*l*). Like the amylase-positive cell clusters, the secretory product was stored in vesicular structures which were concentrated at a cell pole. The presence of secretory cells has been confirmed by electron microscopy, which revealed densely distributed electrodense particles such as those characteristic of excretory or incretory functions (FIG. 6*f-h*).

A differentiation into chondrogenic cells and epithelial cells was also observed. After a growth period of two months, organoid bodies exhibited chondrogenic properties. Alcian blue staining revealed regions with high concentration of proteoglycans (chondroitin sulfate) occurring either as globular deposits (FIG. 5*a*) or as fibrillary deposits (FIG. 5*b*). Immunohistochemical staining with antibodies directed against the cartilage matrix protein collagen II additionally proved the chondrogenic activity within these globular regions (FIG. 5*c*) and fibrillary regions (FIG. 5*d*). The immunoreactivity was highest at the center of the cellular aggregates which most likely corresponded to regions of developing extracellular cartilage matrix. This observation was confirmed by confocal microscopy (FIG. 5*g*): while the quantity of collagen deposits increased toward the center of the cellular aggregates, the border areas were characterized by actively translating cells, as demonstrated by their high expression of vigilin, which is usually found in cells having an active translational machinery, e.g., collagen-synthesizing chondrocytes or in fibroblasts during chondroinduction. Typical individual collagen II-translating chondrocytes have also been observed in out-growing cells of organoid bodies that produce a matrix that contains collagen II and surrounds the individual cells (FIG. 5*e*). An ultrastructure investigation of these regions has clearly revealed a network of reticular fibers and collagen fibers, the latter being identified by their characteristic band pattern (FIG. 6*e*). Some cells also expressed, in addition to mesenchymal markers, multiple cytokeratins, indicating their potential for differentiation into epithelial cells. However, cells that were immunoreactive for cytokeratins were found less frequently than cells that expressed the markers of smooth muscle cells and neurons. Typically they were arranged in clusters disseminated within the organoid bodies (FIG. 5*f*). By electron microscopic examinations, typical cells contacts between keratinocytes were found (FIG. 6*j*) and in eight-week-old organoid bodies epithelial cells were found on the surface growing out of the cell culture medium and into the air.

On the whole, for example, the following markers for specific cells have so far tested positive: PGP 9.5 and NF for nerve cells, S 100 and GFAP for glial cells, SMA for muscle cells (and/or myofibroblasts), collagen type II for cartilage cells, amylase and trypsin for exocrine glandular cells, insulin for endocrine glandular cells, vigilin for strongly translating cells and cytokeratin for epidermal cells. In addition to the light microscopic examinations, electron microscopy was also performed in order to morphologically characterize the various cell types and cell-cell contacts were found as signs of cellular interactions.

So far smooth muscle cells, neurons, glial cells, epithelial cells, fatty cells, heart cells, kidney cells, fibroblasts (e.g., skin and tendon fibroblasts), chondrocytes, endocrine and exocrine glandular cells and thus cell types of all three germ layers have been detected.

In the following nonrestrictive examples, the present invention will be illustrated in greater detail.

The general working procedures which are conventionally used for methods of culturing animal cells and especially mammalian cells are to be observed. A sterile environment in which the process is to be carried out must also be maintained in any case—even if there is no further description in this regard. The following buffers and media were used:

| | |
|---|---|
| HEPES stock solution (pH 7.6) | 2.383 g HEPES to 100 mL double distilled water |
| HEPES Eagle medium (pH 7.4) | 90 mL modified Eagle medium (MEM) 10 mL HEPES stock solution |
| Isolation medium (pH 7.4) | 32 mL HEPES Eagle medium 8 mL 5% BSA in double distilled water 300 μL 0.1 M CaCl$_2$ 100 μL Trasylol (200,000 KIU) |
| Digestion medium (pH 7.4) | 20 mL isolation medium 4 mL collagenase (collagenase NB 8 from Serva) |
| Incubation medium | Dulbecco's modified Eagle medium (DMEM) |
| Culture medium | Dulbecco's modified Eagle medium (DMEM) DMEM + 4500 mg/L glucose + L-glutamine + pyruvate = 20% FCS (inactivated) + 1 mL/ 100 mL penicillin/ streptomycin (10,000 U/10,000 μg/mL) or DMEM + 10% autologous plasma + 1 mL/100 mL penicillin/ streptomycin heat to 37° C. before use |
| Differentiation medium | 380 mL DMEM 95 mL FCS inactivated for 30 minutes at 54° C. 5 mL glutamine (Gibco BRL) 5 mL (3.5 μL β-mercaptoethanol to 5 mL PBS) 5 mL nonessential amino acids (Gibco BRL) 5 mL penicillin/streptomycin (Gibco BRL) (10,000 U/10,000 μg/mL) |

Instead of fetal calf serum (FCS) in the culture medium and differentiation medium, autologous plasma may also be used or, less preferably, autologous serum of the tissue donor. This is important in particular when the tissue donor is identical to the subsequent recipient of the stem cells or differentiated cells derived therefrom. Such an autologous treatment is preferred in order to prevent a possible rejection reaction.

The culture medium may also contain, instead of the DMEM medium, another basic medium suitable for culturing eukaryotic cells, in particular mammalian cells, in which the differentiated cells die and the desired stem cells proliferate. Isolation medium, incubation medium and differentiation medium may also contain a different common and suitable basic medium.

The following Examples 1 and 2 describe in detail two working protocols for isolation and culturing of adult pluripotent stem cells from acinar tissue of the pancreas. Example 3 describes a corresponding protocol for isolation from acinar and tubular tissue of the salivary gland.

EXAMPLE 1

1. Preparation of the Tissue and Isolation of the Cells

Using a syringe and a blunt cannula, 10 mL digestion medium was injected slowly and without bubbles into the pancreatic duct of two- to three-year-old rats. The entire pancreas is inflated by this procedure and thus, can be removed and prepared more easily. The pancreas is then transferred to a glass beaker and another 5 mL digestion medium is added. After removing the fatty tissue and lymph nodes, the tissue is divided very finely in the glass beaker using fine scissors, fatty tissue floating at the top is removed by suction and the suspension is then gassed with carbogen for one minute (repeating if necessary) and incubated for 20 minutes at 37° C., covered with aluminum foil, in an agitator at 200 cycles per minute. Then the medium is cautiously removed with suction, the tissue is divided again using scissors and the tissue fragments are washed twice each with 10 mL isolation medium and then 5 mL digestion medium is again added to the tissue.

After gassing with carbogen again for about one minute and incubating for 15 minutes at 37° C. in an agitator at 200 cycles per minute, the tissue fragments are divided by successively drawing out into a 10 mL, 5 mL, 2 mL and then a 1 mL glass pipette and pressed through a single layer of filter cloth. The cells isolated in this way are then washed five times in incubation medium (37° C.), gassed with carbogen and centrifuged for 5 minutes each time at 90 g. The pellet obtained finally is resuspended in incubation medium, gassed and distributed on tissue culture dishes.

2. Culturing the Cells

The tissue culture dishes with the isolated cells are cultured in an incubator at 37° C. and 5% CO$_2$. The medium is changed every 2 to 3 days, at which time all the differentiated cells are removed.

On the 7$^{th}$ day in the culture, the cells are passaged using a solution consisting of 2 mL PBS, 1 mL trypsin and 2 mL incubation medium. In the course of this, the cells are detaching from the bottom of the culture dish. The cell suspension is centrifuged for five minutes, the supernatant is removed with suction and the cells are resuspended in 2 mL incubation medium, transferred to a medium-sized cell culture flask and 10 mL incubation medium is added. The medium is changed every three days.

On the 14$^{th}$ day in culture, the cells are passaged again, but this time with 6 mL PBS, 3 mL trypsin and 6 mL incubation medium. The cell suspension is centrifuged for five minutes, the supernatant is removed with suction and the cells are resuspended in 6 mL incubation medium, transferred to three medium-sized cell culture flasks and 10 mL incubation medium is added to each.

The cells are cultured further and passaged and seeded until the cells achieve a semiconfluent to confluent state.

EXAMPLE 2

Pancreatic acini were obtained from male Sprague-Dawley rats (20 to 300 g) which had been anesthetized ($CO_2$) and exsanguinated through the dorsal aorta. A cannula was introduced transduodenally into the pancreatic duct and 10 mL digestive medium containing HEPES Eagle medium (pH 7.4), 0.1 mM HEPES buffer (pH 7.6), 70% (v/v) modified Eagle medium), 0.5% (v/v) Trasylol (Bayer AG, Leverkusen, Germany), 1% (w/v) bovine serum albumin), 2.4 mM $CaCl_2$ and collagenase (0.63 P/mg, Serva, Heidelberg, Germany) was injected into the pancreas posteriorly.

Before removing the pancreas it was partially freed of adhering fatty tissue, lymph nodes and blood vessels. Then healthy pancreatic tissue was placed in the digestive medium (at 20° C., lower metabolism), the pancreatic tissue was divided very finely with scissors, fatty tissue floating at the top was removed with suction and the tissue suspension was gassed with Carbogen (Messer, Krefeld, Germany) without allowing the nozzle to enter the medium with the cells (reducing mechanical stress) and the pH was adjusted to 7.4 in this way. Then the suspension was incubated at 37° C. in 10 mL digestion medium in a 25 mL Erlenmeyer flask (covered with aluminum foil) while agitating constantly (150 to 200 cycles per minute). After 15 to 20 minutes, the fat floating at the top and the medium were removed with suction and the tissue was divided again and rinsed with medium without collagenase (repeating the process at least twice, preferably until the cell fraction became transparent), whereupon digestive medium was added and the mixture was gassed again for about one minute with Carbogen. Digestion was again performed with collagenase for 15 minutes at 37° C. in an agitator using the same buffer. After digestion, the acini were dissociated by successively pulling out and ejecting through 10 mL, 5 mL and 2 mL glass pipettes with narrow openings and filtered through a single layer nylon mesh (Polymon PES-200/45, Angst & Pfister A G, Zurich, Switzerland) with a mesh of approximately 250 μm. The acini were centrifuged (at 37° C. and 600 to 800 rpm in a Beckman GPR centrifuge corresponding to approximately 50 to 100 g) and purified further by washing in incubation medium containing 24.5 mM HEPES (pH 7.5), 96 mM NaCl, 6 mM KCl, 1 mM $MgCl_2$, 2.5 mM $NaH_2PO_4$, 0.5 mM $CaCl_2$, 11.5 mM glucose, 5 mM sodium pyruvate, 5 mM sodium glutamate, 5 mM sodium fumarate, 1% (v/v) modified Eagle medium, 1% (w/v) bovine serum albumin, equilibrated with Carbogen and adjusted to a pH of 7.4. The washing procedure (centrifugation, suction removal, resuspension) was repeated five times. Unless otherwise indicated, the isolation procedure described above was performed at approximately 20° C.

The acini were resuspended in incubation medium and cultured at 37° C. in a humid atmosphere with 5% $CO_2$. The acinar tissue died rapidly under these conditions (within 2 days) and the dying differentiated cells separated from the adjacent cells without damaging the latter (gentle isolation) while the non-dying stem cells sank to the bottom and attached themselves. The differentiated acini cells are not capable of doing this. The incubation medium was changed for the first time on the second or third day after inoculating, with most of the freely floating acini and acinar cells being removed. At this point the first stem cells or their precursors had attached themselves to the bottom and had begun to divide. Then the medium was changed again every third day and differentiated acinar pancreatic cells were removed each time the medium was changed.

On the seventh day in culture the cells were passaged with a solution consisting of 2 mL PBS, 1 mL trypsin (+0.05% EDTA) and 2 mL incubation medium, whereupon the cells detached from the bottom of the culture dish. The cell suspension was centrifuged for five minutes at about 1000 rpm (Beckmann GPR centrifuge), the supernatant was removed with suction and the cells were resuspended in 2 mL incubation medium, transferred to a medium-sized cell culture flask and 10 mL incubation medium was added.

On the $14^{th}$ day in culture, the cells again were passaged, but this time with 6 mL PBS, 3 mL trypsin/EDTA and 6 mL incubation medium. The cell suspension was centrifuged for 5 minutes at 1000 rpm, the supernatant was removed with suction and the cells were resuspended in 6 mL incubation medium, transferred to three medium-sized cell culture flasks and 10 mL incubation medium was added to each.

On day 17 a third passage was performed on a total of six medium-sized cell culture flasks, and on day 24 a fourth passage was performed on a total of 12 medium-sized cell culture flasks. Now at the latest all the primary cells were removed from the cell culture except for the stem cells.

The stem cells may be cultured further, passages and inoculations being performed as frequently as desired. The inoculation is preferably performed in a density of $2 \times 10^5$ to $4 \times 10^5$ cells/$cm^2$ in incubation medium.

EXAMPLE 3

Isolation and culturing from exocrine tissue of the parotid gland were performed by analogy with the pancreas protocol with the following deviations:

1. The exocrine tissue of the parotid gland was a mixture of acinar tissue and tubular tissue.

2. Since salivary glands contain less proteases and amylases than the pancreas, it is possible to store the salivary glandular tissue for a while under refrigeration at about 4° C. before workup without damaging the tissue too much. In the concrete example, the storage time was 15 hours and did not have any negative effects with regard to isolation of the desired stem cells.

Example 4 and 5 below describe in detail two protocols for producing organoid bodies and differentiated cells.

EXAMPLE 4

The undifferentiated cells were trypsinated with a solution of 10 mL PBS, 4 mL trypsin and 8 mL differentiation medium and then centrifuged for five minutes. The resulting pellet is resuspended in differentiation medium so that a dilution of 3000 cells per 100 μL medium is established. Then the cells are suspended again well with a 3 mL pipette.

The cover is removed from bacteriological petri dishes that had previously been coated with 15 mL PBS (37° C.) per plate and the cover is inverted. Using an automatic pipette, approximately fifty 20 μL drops are placed on each cover. The cover is then turned over rapidly and placed on the petri dish filled with differentiation medium so that the drops hang down. The petri dishes are then cautiously placed in the incubator and incubated for 48 hours.

Next the aggregated cells in the hanging drops, which should be referred to here as organoid bodies (OB) are transferred from four covers each into one bacteriological petri dish with 5 mL incubation medium with 20% FCS and cultured for another 96 hours.

The organoid bodies are then cautiously collected with a pipette and transferred to cell culture vessels holding differentiation medium and coated with 0.1% gelatin. In an especially preferred embodiment of this method, 6 cm petri dishes coated with 0.1% gelatin are used as the culture vessels; 4 mL differentiation medium is placed in each in advance and then they are charged with six organoid bodies each. Another preferred culture vessel consists of chamber slides coated with 0.1% gelatin with 3 mL differentiation medium placed in each and then charged with three to eight organoid bodies each. In addition, 24-well microtiter plates coated with 0.1% gelatin with 1.5 mL differentiation medium placed in each well and then charged with four organoid bodies each may also be used.

When cultured in this way, the ability of the cells to differentiate into organoid bodies is activated and the cells differentiate into cells of the three germ layers mesoderm, endoderm and ectoderm. The cells may be stored and cultured both as organoid bodies or as individual cells and they retain their pluripotency.

EXAMPLE 5

For induction of differentiation, preferably stem cells after the $42^{nd}$ day of culturing were used. It is also possible to use stem cells after the third or fourth passage or cells stored for 12 to 18 months at the temperature of liquid nitrogen with no problem.

First the cells were transferred to differentiation medium having the composition given above and adjusted to a density of approximately $3\times10^4$ cells/mL, e.g., by trypsin treatment of a stem cell culture in culture medium, centrifugation for 5 minutes at 1000 rpm and resuspending the pellet in differentiation medium and diluting as much as necessary.

Then using a 20 µL pipette, approximately fifty 20 µL drops (600 cells/20 µL) were placed on the inside of the cover of a bacteriological petri dish (stoppered tip) and the covers were cautiously inverted over the petri dishes filled with PBS so that the drops would hang down. A new tip was used for each cover. The petri dishes were then cautiously placed in the incubator and incubated for 48 hours at 37° C.

Next the aggregated cells in the hanging drops, i.e., the organoid bodies (OB), were transferred from four covers each into one bacteriological petri dish each with 5 mL incubation medium with 20% FCS (hold the cover obliquely and rinse off the organoid bodies with approximately 2.5 mL culture medium) and then cultured for five to nine more days, preferably 96 hours.

The organoid bodies were then collected cautiously using a pipette and transferred to cell culture vessels coated with 0.1% gelatin and containing differentiation medium. The organoid bodies would then proliferate and grow into partly isolated cell colonies which could then be further proliferated, isolated and proliferated again. In an especially preferred embodiment of this method, 6 cm petri dishes which were coated with 0.1% gelatin and into which 4 mL differentiation medium had already been placed were used as the culture vessels, each petri dish being charged with six organoid bodies. Another preferred culture vessel was chamber slides coated with 0.1% gelatin, into which 3 mL differentiation medium had been placed and which were then each charged with three to eight organoid bodies, and Thermanox plates (Nalge Nonc International, USA) for electron micrographic studies. Another alternative was 24-well microtiter plates coated with 0.1% gelatin with 1.5 mL differentiation medium placed in each well which was then charged with four organoid bodies each.

In a preferred embodiment of this method, organoid bodies were cultured for about 7 weeks in the gelatin-coated 6 cm petri dishes and then individual organoid bodies were cut out using the Microdissector (Eppendorf, Hamburg, Germany) according to the manufacturer's instructions and then transferred to fresh 6 cm petri dishes, chamber slides or Thermanox plates, for example.

EXAMPLE 6

For isolation and culturing of human adult stem cells, human tissue from adult patients was obtained immediately after a surgical procedure and was worked up immediately. Healthy tissue was separated from the tissue that had been excised surgically, e.g., pancreatic or salivary gland tissue, and placed in digestion medium. This tissue was then worked up according to the protocol described for the rat and the stem cells were isolated and cultured by a similar method.

If the stem cells are to be used later for therapeutic purposes, various conditions must also be met for safety reasons in order to rule out the possibility of a risk to the patient who is to be treated, in particular:

Using human serum, preferably autologous plasma from the patient, instead of FCS, purifying the serum and/or plasma if necessary.

Excluding any animal source for other media additives.

Ultrahigh purity of all substances, sterility of equipment and environment.

Sterility and purity of the stem cells culture by repeated passages of the stem cells and monitoring for contamination by mycoplasma or other microorganisms.

Carefully inspecting the source tissue and the stem cells for tumorgenicity.

EXAMPLE 7

Characterization of Differentiated Cells

1. Immunohistochemistry

Organoid bodies that had been cultured for at least 3 weeks on chamber slides and cross sections of "long-term" organoid bodies were rinsed twice in PBS, fixed for 5 minutes with methanol:acetone (7:3) containing 1 g/mL DAPI (Roche, Switzerland) at −20° C. and washed three times in PBS. After incubation in 10% normal goat serum at room temperature for 15 minutes, the samples were incubated overnight with primary antibodies at 4° C. in a humidification chamber. The primary antibodies were directed against the protein gene product 9.5 (PGP 9.5, polyclonal rabbit antibody, 1:400, Ultraclone, Isle of Wight), neurofilaments (NF-Pan cocktail, polyclonal rabbit antibody, 1:200, Biotrend, Germany), α-smooth muscle actin (α-SMA, monoclonal mouse antibody, 1:100, DAKO, Denmark), glial fibrillary acid protein (GFAP, monoclonal mouse antibody, 1:100, DAKO, Denmark), collagen II (monoclonal mouse antibody II-II-6B3, 1:20, Developmental Studies Hybridoma Bank, University of Iowa, USA), vigilin FP3 (1:200, Kügler et al., 1996), cytokeratins (pan cytokeratin, monoclonal mouse antibody, 1:100, Sigma, USA), α-amylase (polyclonal rabbit antibody 1:100, Calbiochem, Germany) and insulin (monoclonal mouse antibody, 0.5 g/mL, Dianova, Germany). After rinsing three times with PBS, the microscope slide was incubated for 45 minutes at 37° C. with either Cy3-labeled anti-mouse IgG or FITC-labeled anti-rabbit IgG (Dianova), each diluted 1:200. The microscope slides were washed three times in PBS, coated with Vectashield Mounting Medium (Vector, USA) and analyzed with a fluorescence microscope (Axiosop Zeiss, Germany) or with a confocal laser scanning microscope (LSM 510, Zeiss, Germany). Alcian blue staining was performed by standard methods.

2. Transmission Electron Microscopy

Organoid bodies were cultured for at least three weeks on Thermanox plates (Nalge Nonc International, USA). Samples adhering to the Thermanox plates were incubated for 24 hours at a pH of 7.4 by immersing in 0.1M cacodylate buffer containing 2.5% glutaraldehyde and 2% paraformaldehyde. After fixing again in 1% $OSO_4$, "en bloc" staining was performed with 2% uranyl acetate and dehydrogenation in pure alcohols, then the samples were embedded in araldite. After removing the Thermanox plate, semithin sections were made either tangentially or perpendicularly to the embedded cell culture and were then stained with methylene blue and azure II. Ultrathin sections were cut out of the regions of interest, stained with lead citrate and examined using a transmission electron microscope (Phillips, EM 109).

What is claimed is:

1. A composition consisting of isolated pluripotent adult stem cells obtained from an exocrine glandular tissue of a salivary gland, a lacrimal gland, a sudoriferous gland, a sebaceous gland and/or gastrointestinal tissue, wherein the exocrine glandular tissue originates from a mammal, wherein the process for producing the isolated pluripotent adult stem cells comprises:
   removal of exocrine glandular tissue;
   the tissue thus removed is divided in such a gentle way that cell structures in resulting tissue fragments are largely preserved;
   the divided tissue is cultured in a culture medium in the absence of additional specific growth factors or differentiation factors, whereby most of the differentiated cells become detached from the stem cells, whereupon the stem cells adhere on a bottom of a tissue culture vessel;
   the remaining tissue and nonadherent differentiated cells are largely separated by a first change of medium and the remaining nonadherent cells are separated by additional changes of medium at intervals of about 2 to 3 days; and isolating the pluripotent adult stem cells,
   further wherein the isolated pluripotent adult stem cells are capable of differentiating into cell types of all three germ layers in a culture medium that does not contain any additional growth factors or differentiation factors after culturing under spatial conditions which ensure three dimensional contact of the cells.

2. The composition according to claim 1, wherein the exocrine glandular tissue is acinar tissue.

3. The composition according to claim 2, wherein the acinar tissue is derived from the pancreas, the parotid gland or the mandibular gland.

4. A stem cell culture consisting of the composition according to claim 1 in a culture medium adapted to allow stable maintenance and proliferation of the cells essentially without differentiation.

5. The stem cell culture according to claim 4, wherein the culture medium does not include any feeder cell layer.

6. A primary stem cell culture obtained from exocrine glandular tissue from a salivary gland, a lacrimal gland, a sudoriferous gland, a sebaceous gland and/or gastrointestinal tissue of a mammal, wherein living cells from the exocrine glandular tissue present in the culture consist essentially of undifferentiated pluripotent adult stem cells.

7. The primary stem cell culture according to claim 6, wherein the living cells present in the culture consist of undifferentiated pluripotent adult stem cells.

8. The primary stem cell culture according to claim 6, wherein the exocrine glandular tissue is acinar tissue.

9. The primary stem cell culture according to claim 8, wherein the acinar tissue is derived from the pancreas, the parotid gland or the mandibular gland.

10. The primary stem cell culture according to claim 6, wherein the mammal is a primate or a rodent.

11. The primary stem cell culture according to claim 6, wherein the mammal is a human.

12. The primary stem cell culture according to claim 6, wherein the mammal is a rat.

13. The composition according to claim 1, wherein the mammal is a primate or a rodent.

14. The composition according to claim 1, wherein the mammal is a human.

15. The composition according to claim 1, wherein the mammal is a rat.

16. A primary stem cell culture obtained from exocrine glandular tissue from a salivary gland, a lacrimal gland, a sudoriferous gland, a sebaceous gland and/or gastrointestinal tissue of a mammal, wherein living cells from the exocrine glandular tissue present in the culture consist essentially of undifferentiated adult stem cells which are capable of differentiating into cells of all three germ cell layers, wherein the process for producing the isolated pluripotent adult stem cells comprises:
   removal of exocrine glandular tissue;
   the tissue thus removed is divided in such a gentle way that cell structures in resulting tissue fragments are largely preserved;
   the divided tissue is cultured in a culture medium in the absence of additional specific growth factors or differentiation factors, whereby most of the differentiated cells become detached from the stem cells, whereupon the stem cells adhere on a bottom of a tissue culture vessel;
   the remaining tissue and nonadherent differentiated cells are largely separated by a first change of medium and the remaining nonadherent cells are separated by additional changes of medium at intervals of about 2 to 3 days; and isolating the pluripotent adult stem cells,
   further wherein the isolated pluripotent adult stem cells are capable of differentiating into cell types of all three germ layers in a culture medium that does not contain any additional growth factors or differentiation factors after culturing under spatial conditions which ensure three dimensional contact of the cells.

17. The primary stem cell culture according to claim 16, wherein the living cells present in the culture consist of undifferentiated adult stem cells which are capable of differentiating into cells of all three germ cell layers.

18. The primary stem cell culture according to claim 16, wherein the exocrine glandular tissue is acinar tissue.

19. The primary stem cell culture according to claim 18, wherein the acinar tissue is derived from the pancreas, the parotid gland or the mandibular gland.

20. The primary stem cell culture according to claim 16, wherein the mammal is a primate or a rodent.

21. The primary stem cell culture according to claim 16, wherein the mammal is a human.

22. The primary stem cell culture according to claim 16, wherein the mammal is a rat.

23. A composition consisting of isolated pluripotent adult stem cells obtained from an exocrine glandular tissue of a salivary gland, a lacrimal gland, a sudoriferous gland, a sebaceous gland and/or gastrointestinal tissue, wherein the exocrine glandular tissue originates from a mammal, wherein the process for producing the isolated pluripotent adult stem cells comprises:
- removal of exocrine glandular tissue;
- the tissue thus removed is divided in such a gentle way that cell structures in resulting tissue fragments are largely preserved;
- the divided tissue is cultured in an incubation medium in the absence of specific growth factors or differentiation factors, whereby most of the differentiated cells become detached from the stem cells, whereupon the stem cells adhere on a bottom of a tissue culture vessel;
- the remaining tissue and nonadherent differentiated cells are largely separated by a first change of medium and the remaining nonadherent cells are separated by additional changes of medium at intervals of about 2 to 3 days; and
- isolating the pluripotent adult stem cells,
- further wherein the isolated pluripotent adult stem cells are capable of differentiating into cell types of all three germ layers in a culture medium that does not contain any additional growth factors or differentiation factors after culturing under spatial conditions which ensure three dimensional contact of the cells.

24. A primary stem cell culture obtained from exocrine glandular tissue from a salivary gland, a lacrimal gland, a sudoriferous gland, a sebaceous gland and/or gastrointestinal tissue of a mammal, wherein living cells from the exocrine glandular tissue present in the culture consist essentially of undifferentiated adult stem cells which are capable of differentiating into cells of all three germ cell layers, wherein the process for producing the isolated pluripotent adult stem cells comprises:
- removal of exocrine glandular tissue;
- the tissue thus removed is divided in such a gentle way that cell structures in resulting tissue fragments are largely preserved;
- the divided tissue is cultured in an incubation medium in the absence of specific growth factors or differentiation factors, whereby most of the differentiated cells become detached from the stem cells, whereupon the stem cells adhere on a bottom of a tissue culture vessel;
- the remaining tissue and nonadherent differentiated cells are largely separated by a first change of medium and the remaining nonadherent cells are separated by additional changes of medium at intervals of about 2 to 3 days; and
- isolating the pluripotent adult stem cells,
- further wherein the isolated pluripotent adult stem cells are capable of differentiating into cell types of all three germ layers in a culture medium that does not contain any additional growth factors or differentiation factors after culturing under spatial conditions which ensure three dimensional contact of the cells.

25. A composition consisting of isolated pluripotent adult stem cells obtained from an exocrine glandular tissue of a salivary gland, a lacrimal gland, a sudoriferous gland, a sebaceous gland and/or gastrointestinal tissue, wherein the exocrine glandular tissue originates from a mammal, wherein the process for producing the isolated pluripotent adult stem cells comprises:
- removal of exocrine glandular tissue;
- the tissue thus removed is divided in such a gentle way that cell structures in resulting tissue fragments are largely preserved;
- the divided tissue is cultured in an incubation medium plus serum in the absence of additional specific growth factors or differentiation factors, whereby most of the differentiated cells become detached from the stem cells, whereupon the stem cells adhere on a bottom of a tissue culture vessel;
- the remaining tissue and nonadherent differentiated cells are largely separated by a first change of medium and the remaining nonadherent cells are separated by additional changes of medium at intervals of about 2 to 3 days; and
- isolating the pluripotent adult stem cells,
- further wherein the isolated pluripotent adult stem cells are capable of differentiating into cell types of all three germ layers in a culture medium that does not contain any additional growth factors or differentiation factors after culturing under spatial conditions which ensure three dimensional contact of the cells.

26. A primary stem cell culture obtained from exocrine glandular tissue from a salivary gland, a lacrimal gland, a sudoriferous gland, a sebaceous gland and/or gastrointestinal tissue of a mammal, wherein living cells from the exocrine glandular tissue present in the culture consist essentially of undifferentiated adult stem cells which are capable of differentiating into cells of all three germ cell layers, wherein the process for producing the isolated pluripotent adult stem cells comprises:
- removal of exocrine glandular tissue;
- the tissue thus removed is divided in such a gentle way that cell structures in resulting tissue fragments are largely preserved;
- the divided tissue is cultured in an incubation medium plus serum in the absence of additional specific growth factors or differentiation factors, whereby most of the differentiated cells become detached from the stem cells, whereupon the stem cells adhere on a bottom of a tissue culture vessel;
- the remaining tissue and nonadherent differentiated cells are largely separated by a first change of medium and the remaining nonadherent cells are separated by additional changes of medium at intervals of about 2 to 3 days; and
- isolating the pluripotent adult stem cells,
- further wherein the isolated pluripotent adult stem cells are capable of differentiating into cell types of all three germ layers in a culture medium that does not contain any additional growth factors or differentiation factors after culturing under spatial conditions which ensure three dimensional contact of the cells.

\* \* \* \* \*